(12) United States Patent
Botma et al.

(10) Patent No.: US 9,557,343 B2
(45) Date of Patent: *Jan. 31, 2017

(54) DISC DISPENSING DEVICE, TUBULAR CONTAINER FOR USE IN SUCH A DISC DISPENSING DEVICE AND METHOD OF DISPENSING DISCS

(71) Applicant: BD Kiestra B.V., Drachten (NL)

(72) Inventors: Jetze Botma, Drachster Compagnie (NL); Martijn Kleefstra, Surhuisterveen (NL); Trienko Marten Van Der Kaap, Drachten (NL); Martijn Xander Berntsen, Leeuwarden (NL); Jan Bart Van Der Vijver, Groningen (NL)

(73) Assignee: BD Kiestra B.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/671,226

(22) Filed: Mar. 27, 2015

(65) Prior Publication Data

US 2015/0198622 A1 Jul. 16, 2015

Related U.S. Application Data

(63) Continuation of application No. 13/457,812, filed on Apr. 27, 2012, now Pat. No. 8,996,163.

(30) Foreign Application Priority Data

Apr. 29, 2011 (EP) .................................... 11164226

(51) Int. Cl.
*C12M 1/00* (2006.01)
*G01N 35/10* (2006.01)
*C12M 1/36* (2006.01)

(52) U.S. Cl.
CPC .......... *G01N 35/1002* (2013.01); *C12M 41/48* (2013.01); *C12M 99/00* (2013.01); *C12M 99/02* (2013.01)

(58) Field of Classification Search
CPC .......... G07F 11/50; B65H 3/44; B65G 59/02; B65G 59/06; B65G 59/04; C12M 99/00; C12M 99/02; C12M 41/48; G01N 35/1002
See application file for complete search history.

(56) References Cited

U.S. PATENT DOCUMENTS 2,865,156 A 12/1958 Wolfson
3,300,087 A 1/1967 Kuypers
(Continued)

FOREIGN PATENT DOCUMENTS

DE 19521640 A1 1/1997
DE 102004020885 A1 11/2005
(Continued)

OTHER PUBLICATIONS

Examination Report for EP Application No. 11164226.0 dated Sep. 28, 2016.

*Primary Examiner* — Timothy Waggoner
(74) *Attorney, Agent, or Firm* — Lerner, David, Littenberg, Krumholz & Mentlik, LLP

(57) ABSTRACT

Disc dispensing device for dispensing discs impregnated with antibiotics onto a culture dish. The device comprises a stationary support on which a magazine is removably mounted. The magazine holds a plurality of tubular containers each containing a stack of discs to be dispensed. A moving means moves one disc from a bottom end of a tubular container to a pick-up position. From the pick-up position a transfer means picks up said one disc and transfers it to the culture dish where it is dispensed. The removable culture dish is supported by a moveable carriage which is (Continued)

mounted on the stationary support. The carriage is moveable relative to the magazine from a starting position to an operating position and vice versa. Control means control the operation of the device. The plurality of tubular containers is rotatable around a magazine centre under control of the control means.

28 Claims, 1 Drawing Sheet

(56) References Cited

U.S. PATENT DOCUMENTS

| | | | |
|---|---|---|---|
| 3,394,846 A | | 7/1968 | Carski et al. |
| 3,899,011 A | | 8/1975 | Curtiss |
| 3,921,369 A | | 11/1975 | Adams |
| 3,934,753 A | | 1/1976 | Curtiss |
| 4,215,799 A | * | 8/1980 | Swaine ............. G01N 35/1002 221/132 |
| 4,286,730 A | | 9/1981 | Ericsson |
| 5,377,865 A | | 1/1995 | Thomson |
| 5,466,583 A | * | 11/1995 | Thomson ............... C12M 33/00 435/287.1 |
| 7,106,889 B1 | | 9/2006 | Mahers et al. |
| 8,996,163 B2 | * | 3/2015 | Botma .................. C12M 99/02 221/119 |
| 2002/0164676 A1 | | 11/2002 | Shimada et al. |
| 2008/0220465 A1 | | 9/2008 | Ingber et al. |

FOREIGN PATENT DOCUMENTS

| | | |
|---|---|---|
| EP | 1154014 A1 | 11/2001 |
| GB | 905894 A | 9/1962 |
| GB | 2001432 A | 1/1979 |
| GB | 2038771 A | 7/1980 |
| GB | 2411894 A | 9/2005 |
| JP | S55-104897 A | 8/1980 |
| JP | H07-35755 A | 2/1995 |
| JP | 2001149063 A | 6/2001 |
| JP | 2002205804 A | 7/2002 |
| WO | 2006109005 A1 | 10/2006 |
| WO | 2010066562 A1 | 6/2010 |

* cited by examiner

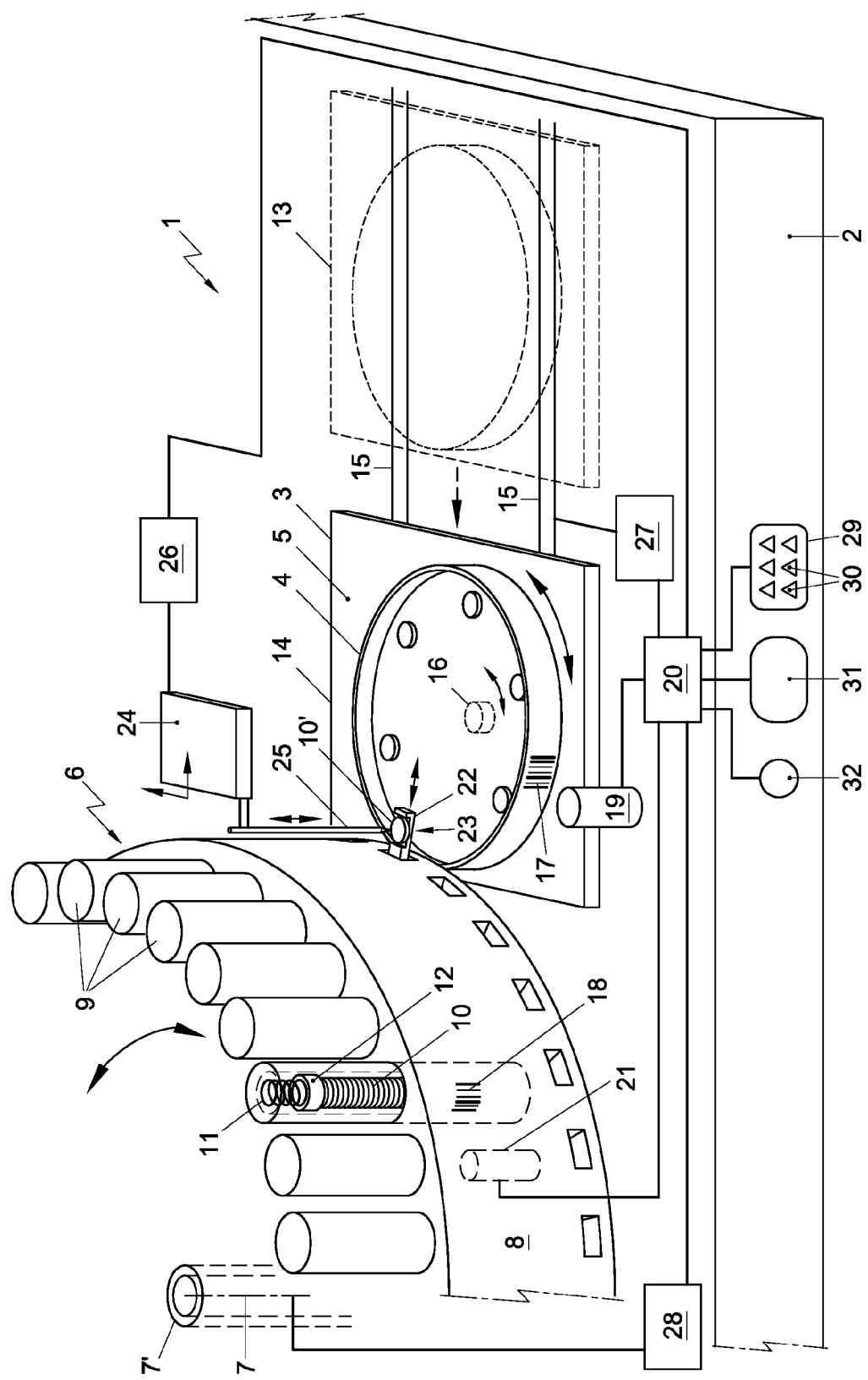

DISC DISPENSING DEVICE, TUBULAR CONTAINER FOR USE IN SUCH A DISC DISPENSING DEVICE AND METHOD OF DISPENSING DISCS

CROSS-REFERENCE TO RELATED APPLICATIONS

The present application is a continuation of U.S. patent application Ser. No. 13/457,812, filed on Apr. 27, 2012, which claims priority from European Patent Application No. 11164226.0 filed Apr. 29, 2011, the disclosures of which are incorporated herein by reference.

TECHNICAL FIELD

The invention relates to a disc dispensing device for dispensing discs impregnated with antibiotics onto a culture dish, said disc dispensing device comprising: a stationary support; a magazine removably mounted on the stationary support, said magazine being arranged for holding a plurality of tubular containers, each tubular container being adapted for containing a stack of discs to be dispensed; moving means for moving one disc from a bottom end of a tubular container to a pick-up position; transfer means for picking up said one disc from the pick-up position, for transferring said one disc to the culture dish and for dispensing said one disc onto the culture dish; a moveable carriage for supporting a removable culture dish, said moveable carriage being mounted on the stationary support and being moveable relative to the magazine from a starting position to an operating position and vice versa; and control means for controlling the operation of the moving means and the operation of the transfer means, said control means being activated to control the moving means and the transfer means to dispense a disc impregnated with antibiotics onto the culture dish in the operating position of the carriage.

BACKGROUND OF THE INVENTION

Such disc dispensing devices may be used in antibiotic susceptibility testing, the agar gel in the culture dish acting as a sterile nutrient medium for a bacteria colony being analysed. The bacteria colony is introduced onto the surface of the gel, usually coming from an original petri dish (preferably after incubation), and the discs are distributed over the surface of the gel by means of the disc dispensing device. Each disc contains a different antibiotic or an antibiotic in a different concentration, so that the effect on the bacteria colony of a plurality of different antibiotics or different concentrations of antibiotics can be simultaneously studied. The use of impregnated discs in this way is well known and will not be described further. In addition, as is usual in this technical field, a bacteria colony normally is put in suspension and brought at the desired concentration before it is transferred to the culture dish. For the sake of simplicity throughout this application the expression bacteria colony is used, but it will be clear to a person skilled in the art that this term refers to any form in which a bacteria colony can be brought which is suitable to transfer to a culture dish. In addition, although the expression "disc" is used throughout this application, this expression in the meaning of this application also refers to discs having a substantial thickness, and thus also encompasses tablets impregnated with antibiotics. In addition the discs need not have a uniform thickness.

A disc dispensing device of the kind as described above is known from GB-A-2 001 432. In this known device the discs are stacked one on top of another in a plurality of elongate cylindrical cartridges provided in a magazine. The discs are biased to an exit end of the cartridge by means of an internal coil spring. Any one cartridge contains only discs impregnated with one particular antibiotic, details of which are displayed on the exterior of the cartridge. A culture dish can be placed on a moveable carriage which is moved in an operating position which is at least almost directly positioned underneath the magazine. After manually positioning the culture dish in the starting position and manually positioning the cartridge in the device the known dispensing device further operates almost completely automatic and consequently provides a preparation for a rapid analysis of clinical samples, thus facilitating its use in situations such as hospitals and laboratories where a considerable number of tests must be made. In the known device a disc is transferred by applying suction to a transfer pipe to thereby hold a disc on the free end of the pipe. The pipe is moved so that the disc is transferred with the pipe from the pick-up position to a releasing position. Upon termination of the suction applied to the pipe the disc is released on the culture dish. Although this known disc dispensing device can operate satisfactorily the internal construction of the magazine and the suction device to transfer discs from a respective cartridge to a specified position on the culture disc is complex and only provides a limited choice in dispensing positions of discs on the culture dish. Furthermore, adaptation of the known disc dispensing device to a different bacteria colony present on the culture dish is relatively time consuming, in particular replacing the magazine and replacing the cartridges within the magazine is time consuming.

SUMMARY OF THE INVENTION

It is an object of the invention to provide a simple and compact disc dispensing device, which can be used in a versatile way and which can be adapted quickly to changes in bacteria colonies (in particular changes in the identity of the bacteria colonies) present on a culture dish.

According to the invention at least one of these objects or at least part of one of these objects is achieved by providing a disc dispensing device for dispensing discs impregnated with antibiotics onto a culture dish according to claim 1. Since the plurality of containers is rotatable around a magazine centre under control of the control means it is possible to simplify the construction of the disc dispensing device.

In an embodiment of a disc dispensing device according to the invention the operating position is spaced from the centre of the magazine. By spacing the operating position from the centre of the magazine, the culture dish can be positioned at such a distance from the magazine that handling and operation, and consequently construction, can be simplified. In addition since there is more space available, additional devices can be positioned on the stationary support. For example, it is thus possible to position more carriages around the magazine, such that a plurality of culture dishes can be used at the same time. In addition it is thus possible to use a very large number, e.g. forty-two, of tubular containers and still be able to dispense discs in a relatively easy manner on the culture dish. Such a large number of containers allows a vast number of combinations of discs, and consequently antibiotics to be used in a susceptibility test, with one and the same magazine. It is in particular advantageous when the moving means is a moving means for moving one disc from a bottom end of a tubular container to a pick-up position in a radial direction outwardly from the centre of the magazine.

In a further embodiment of a disc dispensing device according to the invention the pick up position is fixed relative to the stationary support. In this way it is possible to use a transfer means which is relatively simple of construction. Alternatively the pick up position is displaceable relative to the stationary support, but this also entails a displaceable transfer means.

In order to be able to provide a distributed placement of discs on the culture dish the carriage comprises in an embodiment of a disc dispensing device according to the invention means for rotating the culture disc. In this way the culture dish can be rotated so that a number of discs can be positioned at desired positions on the culture dish. In particular when the transfer means comprises a needle and displacing means for displacing the needle in at least one dimension, preferably at least two dimensions and most preferable three dimensions, the discs can be positioned at any place on the culture dish. In order to assist the release of a disc from the needle the needle may be surrounded by a sleeve which is moveable relative to the needle.

In order to automate the operation as much as possible it is preferred that the disc dispensing device further comprises culture dish identifying means for detecting and reading an identifying mark on a culture dish, said culture dish identifying means being connected to the control means for providing a signal indicative of the read identifying mark of the culture dish to the control means.

Optionally it is advantageous that the disc dispensing device further comprises tubular container identifying means for detecting and reading an identifying mark on a tubular container, said tubular container identifying means being connected to the control means for providing a signal indicative of the read identifying mark of the tubular container to the control means. It is then advantageous when the control means comprises a memory, said control means being adapted for automatically or responsive to manual input activating the tubular identifying means during rotation of the plurality of containers for reading all the tubular container identifying marks, and being adapted for automatically inputting the signals indicative of the read tubular identifying marks into the memory, indicating the position and content of each of the plurality of tubular containers within the magazine, and wherein said control means are adapted for controlling the rotation of the plurality of tubular containers, the rotation of the culture dish, the operation of the moving means and/or the operation of the transfer means based on the input position and content of each of the plurality of tubular containers contained in the memory and based on suitable software programs loaded on a processor of the control means.

Although any known identification means (such as e.g. RFID labels, alphanumerical characters, etc.) can be applied in the inventive device a very reliable and advantageous embodiment of the invention uses a bar code scanner (also called bar code reader) for detecting and reading the culture dish and/or the tubular containers. In this case the identifying mark is of course a bar code.

The culture dish identifying mark may contain information which is relevant for operating the disc dispensing device. Such information may include one or more of the following: the manufacturer of the culture dish, the specific identification number of the culture dish, the agar gel present in the culture dish, the identity of the bacteria colony present in the culture dish, the original petri dish from which the bacteria culture was transferred, the suspension used, the concentration of the bacteria colony, the date when the bacteria colony was transferred to the culture dish, the expiry date before which the culture dish has to be used etc. The tubular container identifying mark may contain information which is relevant for operating the disc dispensing device. Such information may include one or more of the following: the manufacturer of the tubular container, the specific identification number of the tubular container, the number of discs contained in the tubular container, the kind of the antibiotics present in the tubular container, the concentration of the antibiotics in the tubular container, the date when the discs were placed in the tubular container, the expiry date before which the discs have to be used etc. In addition an identifying mark may not contain this information itself but may contain a reference (a so-called key) to a database, another memory or external device from which the relevant information may be obtained.

An embodiment of a disc dispensing device according to the invention can operate in a first automatic operation mode, a so-called stand alone mode, for controlling the rotation of the plurality of tubular containers, the rotation of the culture dish, the operation of the moving means and/or the operation of the transfer means based on the signal indicative of the read identifying mark of the culture dish and/or the signal indicative of the read identifying mark of the tubular container, and based on suitable software programs loaded on a processor of the control means.

Alternatively or additionally the disc dispensing device according to the invention can operate in a second automatic operation mode, a so-called full automatic mode, when the control means comprises a communication interface to an external device for sending and receiving information to and from said external device, respectively. In this second mode the control means is adapted for controlling the rotation of the plurality of tubular containers, the rotation of the culture dish, the operation of the moving means and/or the operation of the transfer means based on the signal indicative of the read identifying mark of the culture dish and/or the signal indicative of the read identifying mark of the tubular container, and based on received external information. In both the first and second operation mode the control means automatically obtains the necessary information to control the operation of the disc dispensing device, and thus it is e.g. possible that automatically a selection of discs (i.e. antibiotics) is made, together with e.g. a specific placement of the discs on the culture dish.

A versatile disc dispensing device is provided in accordance with the invention in case the disc dispensing device comprises a manual control panel, said control means being adapted for operating in a third operation mode in which the control means is overridden by the manual control panel. In this way it is e.g. possible to input in the control panel the number and kind of discs that are to be dispensed on the culture dish, and optionally their position thereon when the control means comprises a memory, and when the control panel is adapted for enabling manual input of the position and content of each of the plurality of tubular containers within the magazine into the memory, and when the control means are adapted for controlling the rotation of the plurality of tubular containers, the rotation of the culture dish, the operation of the moving means and/or the operation of the transfer means based on the input position and content of each of the plurality of tubular containers contained in the memory and based on suitable software programs loaded on a processor of the control means. In this way it is e.g. possible to use tubular containers in the inventive disc dispensing device which do not have identifying marks.

To enable further automation an embodiment of the disc dispensing device of the invention further comprises means for automatically removing and placing a lid from and on a culture dish, respectively, wherein it is advantageous when the disc dispensing device further comprises a conveyor for conveying a culture dish to and from the moveable carriage and means for automatically transferring a culture dish from the moveable carriage onto the conveyor and vice versa, respectively.

The invention further relates to a tubular container for use in a disc dispensing device according to the invention, wherein said tubular container is provided with an identifying mark, said identifying mark being readable by tubular container identifying means, said identifying mark referring to and/or containing information at least regarding the content of the tubular container. The tubular container identifying mark may contain information which is relevant for operating the disc dispensing device or for other purposes. Such information may include one or more of the following: the manufacturer of the tubular container, the specific identification number of the tubular container, the number of discs contained in the tubular container, the kind of the antibiotics present in the tubular container, the concentration of the antibiotics in the tubular container, the date when the discs were placed in the tubular container, the expiry date before which the discs have to be used etc. In addition an identifying mark may not contain this information itself but may contain a reference (a so-called key) to a database, another memory or external device from which the relevant information may be obtained.

The invention also relates to a method of dispensing discs impregnated with antibiotics, said method comprising the steps of:

providing a culture dish in a starting position;

moving said culture dish from the starting position into an operating position;

providing a magazine comprising a plurality of tubular containers, each tubular container containing a stack of discs to be dispensed, when the culture dish is in the operating position moving one disc from a bottom end of a tubular container to a pick-up position, picking up said one disc from the pick-up position, transferring said one disc to the culture dish and dispensing said one disc onto the culture dish, controlling the step of moving said culture dish and the step of transferring said one disc to the culture dish to dispense a disc impregnated with antibiotics onto the culture dish in the operating position, characterized in that the method comprises the step of rotating the plurality of tubular containers around a magazine centre when the culture dish is in the operating position. Preferred embodiments of the inventive method are disclosed in the dependent claims.

The inventive disc dispensing device and the inventive method of dispensing discs provides the possibility to dispense a large number of discs on the culture dish which number is not restricted by the number of tubular containers used. In this manner susceptibility tests can be performed with much more variety and choices of antibiotics.

Further objects, features, effects, advantages and details of the invention are described with reference to examples shown in the drawings

BRIEF DESCRIPTION OF THE DRAWINGS

FIG. 1 schematically shows a disc dispensing device in accordance with the invention.

DETAILED DESCRIPTION

Referring to FIG. 1, an embodiment of the disc dispensing device 1 is shown which comprises a stationary support 2 which is only partly shown.

A moveable carriage 3 is mounted on the stationary support 2 and has a horizontal surface 5 for supporting a removable culture dish 4. A means (not shown) is provided on the carriage 3 for securely locating the culture dish 4 on the horizontal surface 5. The culture dish 4 is intended to contain a thin layer of nutrient agar gel (not shown) onto or into which a bacteria colony under test has previously been seeded or otherwise applied, using known techniques. For example, the bacteria colony can be transferred in a known manner from an original petri dish onto the culture dish 4. The purpose of the disc dispensing device is to deposit onto the surface of this layer of agar gel an array of spaced susceptibility discs, each disc being impregnated with a different antibiotic (in which 'different' can also refer to a different concentration). Once all the desired or required discs have been deposited, the culture dish and its contents are removed and placed in an incubator so that the effect of each antibiotic on the bacteria colony can be assessed. The number of discs and the pattern in which they are placed on the agar gel layer can be selected (to be described later).

The disc dispensing device 1 further comprises a magazine 6 which is removably mounted on the stationary support 2.

During operation of the disc dispensing device 1, a central bore 7' (which in this embodiment forms the centre of the magazine 6) of the magazine 6 is mounted on a vertical axle 7. It can be seen in FIG. 1 that the magazine 6 comprises a substantially circular housing 8. The antibiotic discs to be dispensed are contained in a plurality of individual tubular containers 9. In the present embodiment forty-two tubular containers are arranged and held by the magazine 6. It will be clear however that in other embodiments of the invention other numbers of tubular containers can be received by the magazine, but relatively large numbers, i.e. well above twenty, are preferred. The discs 10 are piled on top of one another in a stack within each tubular container and are e.g. biased towards the lower end of the container by means of a coil spring 11 and plunger 12. The lower or bottom end of the tubular container is in a known manner provided with an opening such that one single disc can be dispensed from the tubular container. Since the magazine 6 is removable it is possible to install different sets of tubular containers containing a wide selection of antibiotics which can be used to perform the susceptibility test. However, in case forty-two tubular containers are used, replacement of the magazine will be seldom necessary. Each tubular container 9 can contain an identifying mark 18, in the shown example a bar code, containing (or referring to) information regarding e.g. the kind of antibiotics, the concentration of the antibiotics, etc. contained therein.

At the beginning of operation the moveable carriage 3 is positioned on the stationary support 2 in a starting position indicated by broken lines. In this starting position 13 a culture dish is placed on the carriage. Although not shown in the Figure a conveyor is present for automatically conveying a culture dish to the moveable carriage, and also means for automatically transferring the culture dish from the conveyor onto the carriage are present. Correct placement of the culture dish on the carriage can e.g. be detected by micro-switches or visually by an operator. After correct placement has been established a lid which is usually placed on the culture dish is automatically removed from the culture dish by (not shown) suitable means. Please note that in alternative embodiments conveyance, transfer and removing a lid can take place manually. After correct placement has been established the carriage can be moved towards the magazine 6 into an operating position 14 (indicated with solid lines). This movement can be performed by any known means, such as for example along rails 15 which are engaged by wheels (not shown) mounted under the carriage. The wheels can be driven under control of control means 20. As clearly can be seen in FIG. 1 the operating position 14 is spaced from the centre 7' of the magazine 6.

In order to be able to for example trace and identify the culture dish 4 and its contents, such as for example the kind of agar gel, the bacteria colony deposited in the culture dish, and the original petri dish, the culture dish 4 is provided with an identifying mark 17, in the shown example a bar code containing the relevant information.

In the shown embodiment the carriage 3 comprises means 16 for rotating the culture dish 4, which means in this example is formed by a rotational shaft 16 on which the culture dish 4 is mounted. The rotational shaft 16 can be activated for giving a rotational movement to the culture dish 4 at any time after the culture dish is correctly positioned on the carriage. In any case the rotational shaft 16 needs to be activated for rotating the culture dish during dispensing of the discs in the culture dish, thus the culture dish is rotatable when the carriage is in the operating position. In addition, the disc dispensing device 1 comprises culture dish identifying means, in this example in the form of a bar code reader 19 which is able to read the bar code 17 on the culture dish 4, for detecting and identifying the culture dish. This bar code reader 19 is connected to a control means 20 for providing a signal indicative of the identity of the culture dish 4 (and other relevant information, such as e.g. its contents) to the control means 20. Depending on the position of the bar code reader 19 on the stationary platform 2 the rotational shaft 16 is activated such that the bar code 17 on the culture dish 4 can correctly be read. In the shown embodiment the bar code reader or scanner 19 is positioned such that it can correctly read the bar code 17 when the culture dish is rotated in the operating position of the carriage 3.

In a similar way the disc dispensing device 1 can further comprise tubular container identifying means, in this example also in the form of a bar code reader or scanner 21, for detecting and identifying the bar code 18 on a tubular container 9. This container bar code reader 21 is suitably positioned inside the housing 8 and provides a signal indicative of the read identifying mark, in this case the bar code, of the tubular container to the control means 20. This signal can also be used to identify the position of the respective tubular container within the magazine 6. Please note that in case the tubular containers are not provided with identifying marks, it is possible to input the relevant information into the control means manually.

It will be clear that although in the described embodiment bar codes and bar code readers are used, it is in other embodiments of the invention possible to use other known identifying marks and mark readers. In addition in case suitably positioned, e.g. in the lower part of the housing 8 and on the outer side thereof only one bar code reader is sufficient to read both the culture dish bar code and the tubular container bar codes.

To dispense a single disc 10' impregnated with antibiotics from a tubular container 9 the disc dispensing device 1 comprises moving means 22 for moving one disc from the lower or bottom end of a tubular container to a pick-up position 23, which is fixed or stationary relative to the stationary support 2. The moving means 22 (which are controlled by the control means 20) linearly moves the one disc in a radial direction outwardly from the centre of the magazine 7' towards the pick up position 23. Although each tubular container can be associated with a respective moving means, it is possible to use one and the same moving means for all the tubular containers.

Since the pick up position 23 is fixed relative to the support 2 transfer means 24 comprising a needle 25 for picking up said one disc from the pick-up position, and for transferring said one disc 10' to the culture dish 4 can also be positioned in a stationary position on the support. The transfer means 24 is controlled by a microprocessor 26 which is controlled by the control means 20 for displacing the needle 25 in at least one dimension (i.e. in this case upward and downward). In this way the needle 25 can be lowered to penetrate the disc 10' and to hold to disc 10'. Thereafter the needle 25 is raised, the moving means 22 is retracted in the direction of the centre of the magazine and the needle 25 is lowered until the disc 10' contacts the agar gel. Since the contact force applied by the agar gel on the disc 10' is larger than the force applied by the needle 25, when raising the needle 25 the disc 10' remains behind in the culture dish. However, in order to assist removal of the disc from the needle a moveable sleeve can be arranged around the needle, which sleeve when lowered, pushes the disc off the needle. In other embodiments transfer means can be used to displace the needle in at least two and preferably in three dimensions, such that a disc can be positioned at any specific location on the culture dish 4, thereby allowing much more discs to be placed in a wide variety, improving susceptibility tests.

In order to dispense the next disc impregnated with antibiotics the plurality of containers 9 is rotated such around the axle 7 that the container containing the next disc is positioned correctly with respect to the transfer means (and in case of an embodiment using one single moving means correctly with respect to this unique moving means). In addition the culture dish is rotated to the next position for receiving this next disc. When the required or desired number of discs is placed on the culture dish, the carriage is moved back to the starting position, optionally an indication (visual or auditory) is given by the disc dispensing device, and the means for automatically removing and placing a lid can put a lid back on the culture dish, whereafter it is automatically transferred to the conveyor for further processing. In alternative embodiments the lid can be put back on the culture disc manually, as well as transferring the culture disc for further processing can take place by an operator in a manual way.

The control means 20 of the disc dispensing device 1 controls the operation of the components of the disc dispensing device. The control means 20 can be formed by any programmable processor device, and the invention is not limited to a specific kind of control means, as long as it is able to perform the required functions.

The control means 20 is connected to drive means 27, which drives the movement of the carriage from the starting position to the operating position and vice versa, and which also activates the rotational shaft 16 in order to rotate the culture dish. Furthermore, the control means 20 is connected to a drive 28 for driving the rotation of the plurality of tubular containers 9 around the axle 7. As mentioned above the control means 20 also controls the operation of the moving means 22, and the operation of the transfer means 24 via the microprocessor 26 to dispense a disc impregnated with antibiotics onto the culture dish in the operating position of the carriage. In addition, as already described above the control means 20 is connected to the bar code readers or scanners 19, 21 to receive information therefrom.

The disc dispensing device 1 comprises a manual control panel 29 comprising a number of control buttons 30, and a visual display 31 for amongst other things displaying operational data to an operator of the disc dispensing device. A communication interface 32 is present to establish communication between the control means and an external device for sending and receiving information to and from said external device, respectively. Such an external device can e.g. be a bacterial colony identification device such as a Maldi-tof mass spectrometry machine or a personal computer.

The disc dispensing device 1 can be operated in at least three different operational modes.

In a first operation mode the control means 20 controls the rotation of the plurality of tubular containers 9, the rotation of the culture dish 4, the operation of the moving means 22 and the operation of the transfer means 24 based on the signals received from the bar code readers 19 and (optionally) 21, which signals are indicative of the identifying mark of the culture dish and of the identifying mark of the tubular container (if present). Based on suitable software programs loaded on a processor of the control means 20, the number of discs, the kind of discs (i.e. the kind of antibiotics), the order of placement of the discs and the pattern (including mutual spacing) in which the discs are placed can be selected. Such suitable software programs are common in the field of susceptibility testing and need no further description. In addition if the tubular containers contain identifying marks the control means control the rotation of the plurality of containers such that they are at least fully rotated once so that all the identifying marks are read and the relevant information is stored in the memory of the control means. Based on this stored information the position of each tubular container within the plurality and its contents is known.

In a second mode of operation the control means 20 receives suitable information via the communication interface 32 from an external device (preferably upon a request sent by the control means 20, in which request information obtained from the read culture dish bar code is contained). This information is used by the control means 20 to control the rotation of the plurality of tubular containers, the rotation of the culture dish, the operation of the moving means and the operation of the transfer means in addition to the signals received from the bar code readers 19 and 21, which signals are indicative of the identity of the culture dish and of the identity of the tubular container. Again based on suitable software programs loaded on a processor of the control means 20, the number of discs, the kind of discs (i.e. the kind of antibiotics), the order of placement of the discs and the pattern (including mutual spacing) in which the discs are placed can be selected in dependence of e.g. the identity of the bacteria colony as received from a Maldi-tof machine. Such suitable software programs are common in the field of susceptibility testing and need no further description.

In a third operation mode the automatic control by the control means 20 is overridden by input via the manual control panel 29. By using the manual control panel 29 an operator can manually input for example at least one of the following: the number of discs, the kind of discs, the order of placement of the discs and the pattern (including mutual spacing) in which the discs are to be placed on the culture dish. Such a manual selection can be performed with and without information from one or both of the bar code scanners.

With the disc dispensing device as described above it thus is possible to perform a method of dispensing discs impregnated with antibiotics, said method comprising the steps of providing a culture dish in a starting position; moving said culture dish from the starting position into an operating position; providing a magazine comprising a plurality of tubular containers, each tubular container containing a stack of discs to be dispensed, when the culture dish is in the operating position moving one disc from a bottom end of a tubular container to a pick-up position, picking up said one disc from the pick-up position, transferring said one disc to the culture dish and dispensing said one disc onto the culture dish, controlling the step of moving and transferring to dispense a disc impregnated with antibiotics onto the culture dish in the operating position, and the step of rotating the plurality of tubular containers around a magazine centre when the culture dish is in the operating position. The operating position can be provided at a position spaced from the centre of the magazine. One disc can be moved from a bottom end of a tubular container to a pick-up position in a radial direction outwardly from the centre of the magazine. The pick up position can be in one stationary spatial position. The culture dish can be rotated. In the method a bacteria colony is transferred from an original petri dish onto the culture dish and an identifying mark, such as a bar code, is provided on the culture dish. In this culture dish identifying mark information is incorporated or a reference or key is incorporated from which at least the original petri dish, the bacteria colony or the identity of the specific culture dish can be deduced. The identifying mark on the culture dish is read and a signal indicative of the read identifying mark of the culture dish is provided. In each one of the plurality of tubular containers discs are provided which are impregnated with an antibiotic having a property which is different from the property of antibiotics used to impregnate the discs contained in the other tubular containers of the plurality. Optionally an identifying mark, such as a bar code, is provided on said tubular container, and in which identifying mark information is incorporated from which at least the kind of antibiotics, the concentration of the antibiotics or the identity of the specific tubular container can be deduced. The tubular container identifying mark is read and a signal indicative of the read identifying mark of the tubular container is provided. Based on the information deducible from the culture dish identifying mark the discs to be dispensed from specific tubular containers are chosen. The number of discs to be dispensed on the culture dish, the tubular containers from which the discs are to be taken and/or the position of each disc on the culture dish can optionally be chosen by manual input. The plurality of tubular containers can be rotated so that all tubular container identifying marks are read during said rotation, after which all the signals of the read identifying marks are stored automatically. The number of discs to be dispensed on the culture dish, the tubular containers from which the discs are to be taken and/or the position of each disc on the culture dish can be chosen based on the signal indicative of the read identifying mark of the culture dish and/or on the signal indicative of the read identifying mark of the tubular container. The inventive method further provides the possibility to request the identity of the bacteria colony from an external system. In the method a lid can automatically be removed from and placed on a culture dish, respectively, whereas also conveying and transferring a culture dish to and from the starting position can be performed automatically.

The invention claimed is:

1. A method of dispensing discs impregnated with antibiotics, said method comprising the steps of:
   providing a culture dish in a starting position;
   moving the culture dish from the starting position into an operating position;
   providing a magazine comprising a plurality of tubular containers, each tubular container containing a stack of discs to be dispensed,
   when the culture dish is in the operating position moving one disc from a bottom end of a tubular container in a radial direction outwardly to a pick-up position,
   picking up the one disc from the pick-up position, transferring the one disc to the culture dish and dispensing the one disc onto the culture dish,
   controlling the step of moving the culture dish and the step of transferring the one disc to the culture dish to dispense a disc impregnated with antibiotics onto the culture dish in the operating position,
   wherein the method comprises the step of rotating the plurality of tubular containers around a magazine centre when the culture dish is in the operating position.

2. The method as claimed in claim 1, further comprising providing the operating position at a position spaced from the centre of the magazine.

3. The method as claimed in claim 1, wherein the radial direction outwardly is from the centre of the magazine.

4. The method as claimed in claim 3 further comprising providing the pick up position in one stationary spatial position.

5. The method as claimed in claim 1, further comprising rotating the culture dish.

6. The method as claimed in claim 5, wherein the method further comprises:
   transferring a bacteria colony from an original petri dish onto the culture dish;
   providing a machine-readable identifying mark on the culture dish wherein the machine-readable identifying mark identifies at least one of the following: i) the original petri dish, ii) the bacteria colony or iii) an identity of the culture dish;
   reading the identifying mark on the culture dish; and
   providing a signal indicative of the read identifying mark of the culture dish.

7. The method as claimed in claim 1, wherein the method further comprises;
   providing in each one of the plurality of tubular containers discs impregnated with an antibiotic having a property which is different from the property of antibiotics used to impregnate the discs contained in the other tubular containers of the plurality;
   providing a machine readable code on each tubular container, the machine readable code identifying: at least one of: i) a kind of antibiotics carried by the discs in the tubular container; ii) a concentration of the antibiotics carried by the discs in the tubular container; and iii) an identity of the specific tubular container;
   reading the tubular container identifying mark; and
   providing a signal indicative of the read identifying mark of the tubular container.

8. The method as claimed in claim 7, wherein, based on the information from the culture dish identifying mark, choosing the discs to be dispensed from the tubular container.

9. The method as claimed in claim 1 further comprising selecting at least one of: i) a number of discs to be dispensed on the culture dish, ii) the tubular containers from which the discs are to be taken; and iii) a position of each disc on the culture dish, wherein selection is made by manual input to a controller that controls dispensing a disc from the tubular container to the culture dish.

10. The method as claimed in claim 7 wherein the method further comprises:
    rotating the plurality of tubular containers;
    reading all tubular container identifying marks during the rotation; and
    automatically storing all the signals of the read identifying marks.

11. The method as claimed in claim 6, in which at least one of: i) a number of discs to be dispensed on the culture dish; ii) the tubular containers from which the discs are to be taken; and iii) a position of each disc on the culture dish is chosen based on one of the signal indicative of the read identifying mark of the culture dish or the signal indicative of the read identifying mark of the tubular container or both.

12. The method as claimed in claim 7, in which at least one of: i) a number of discs to be dispensed on the culture dish; ii) the tubular containers from which the discs are to be taken; and iii) a position of each disc on the culture disc is chosen based on one of the signal indicative of the read identifying mark of the culture dish or the signal indicative of the read identifying mark of the tubular container or both.

13. The method as claimed in claim 11, the method further comprising requesting the identity of the bacteria colony from an external system.

14. The method as claimed in claim 1, wherein a needle is used for picking up the one disc from the pick-up position, transferring the one disc to the culture dish and dispensing the one disc onto the culture dish, wherein the needle is surrounded by a sleeve which is movable relative to the needle.

15. The method as claimed in claim 1, wherein the method further comprises automatically removing from and placing a lid on a culture dish.

16. The method as claimed in claim 1, wherein the method further comprises automatically conveying and transferring a culture dish to and from the starting position.

17. A method of dispensing discs impregnated with antibiotics, said method comprising the steps of:
    providing a culture dish in a starting position;
    moving said culture dish from the starting position into an operating position;
    providing a magazine comprising a plurality of tubular containers, each tubular container containing a stack of discs to be dispensed, the discs being impregnated with an antibiotic composition, wherein the antibiotic composition impregnating the discs in a first tubular container is different from the antibiotic composition impregnating the discs in a second tubular container,
    when the culture dish is in the operating position moving one disc from a bottom end of a tubular container to a pick-up position,
    picking up said one disc from the pick-up position, transferring said one disc to the culture dish and dispensing said one disc onto the culture dish,
    controlling the step of moving said culture dish and the step of transferring said one disc to the culture dish to dispense a disc impregnated with antibiotics onto the culture dish in the operating position,
wherein the method comprises the step of rotating the plurality of tubular containers around a magazine centre when the culture dish is in the operating position and wherein at least one of the culture dish and the tubular container has a machine-readable code thereon.

18. The method of claim 17, further comprising providing the operating position at a position spaced from the centre of the magazine.

19. The method of claim 17, wherein the step of moving one disc from a bottom end of a tubular container to a pick-up position is performed in a radial direction outwardly from the centre of the magazine.

20. The method of claim 19 further comprising providing the pick up position in one stationary spatial position.

21. The method of claim 17 further comprising rotating the culture dish.

22. The method of claim 21, further comprising:
transferring a bacteria colony from an original petri dish onto the culture dish;
providing the machine readable code on the culture dish;
wherein the machine readable code identifies at least one of:
i) the original petri dish;
ii) the bacteria colony; and
iii) an identity of the specific culture dish reading the identifying mark on the culture dish;
providing a signal indicative of the read identifying mark of the culture dish.

23. The method of claim 17 further comprising:
providing in each one of the plurality of tubular containers discs impregnated with an antibiotic having a property which is different from the property of antibiotics used to impregnate the discs contained in the other tubular containers of the plurality;
providing the machine readable code on each tubular container;
the machine readable code identifying at least one of:
i) a kind of antibiotics carried by the discs in the tubular container;
ii) a concentration of the antibiotics carried by the discs in the tubular container; and
iii) an identity of the specific tubular container;
reading the tubular container identifying mark;
providing a signal indicative of the read identifying mark of the tubular container.

24. The method of claim 23, wherein, based on the information from the culture dish identifying mark, choosing the discs to be dispensed from the tubular container.

25. The method of claim 17, further comprising selecting at least one of:
i) a number of discs to be dispensed on the culture dish;
ii) the tubular containers from which the discs are to be taken; and
iii) a position of each disc on the culture dish, wherein selection is made by manual input to a controller that controls dispensing a disc from the tubular container to the culture dish.

26. The method of claim 23, wherein the method further comprises:
rotating the plurality of tubular containers;
reading all tubular container identifying marks during the rotation; and
automatically storing all the signals of the read identifying marks.

27. The method of claim 22, in which at least one of:
i) a number of discs to be dispensed on the culture dish;
ii) the tubular containers from which the discs are to be taken; and
iii) a position of each disc on the culture dish is chosen based on one of the signal indicative of the read identifying mark of the culture dish or the signal indicative of the read identifying mark of the tubular container or both.

28. The method of claim 23, in which at least one of:
i) a number of discs to be dispensed on the culture dish;
ii) the tubular containers from which the discs are to be taken; and
iii) the position of each disc on the culture disc is chosen based on one of the signal indicative of the read identifying mark of the culture dish or the signal indicative of the read identifying mark of the tubular container or both.

* * * * *